(12) United States Patent
Affagard et al.

(10) Patent No.: US 10,736,849 B2
(45) Date of Patent: Aug. 11, 2020

(54) METHOD OF LYOPHILIZATION OF A SAMPLE OF FAECAL MICROBIOTA

(71) Applicants: MAAT PHARMA, Lyons (FR); INSTITUT NATIONAL DE LA RECHERCHE AGRONOMIQUE, Paris (FR)

(72) Inventors: Hervé Affagard, Lyons (FR); Carole Schwintner, Lyons (FR); Catherine Juste, Le Perray-en-Yvelines (FR); Joël Dore, Vitry-sur-Sein (FR); Audrey Chapron, Breuillet (FR); Fernanda Fonseca, Villepreux (FR); Olivier David, Jouy-en-Josas (FR)

(73) Assignees: MAAT PHARMA, Lyons (FR); INSTITUT NATIONAL DE LA RECHERCHE AGRONOMIQUE, Paris (FR)

(*) Notice: Subject to any disclaimer, the term of this patent is extended or adjusted under 35 U.S.C. 154(b) by 130 days.

(21) Appl. No.: 16/063,419

(22) PCT Filed: Dec. 19, 2016

(86) PCT No.: PCT/FR2016/053550
§ 371 (c)(1),
(2) Date: Jun. 18, 2018

(87) PCT Pub. No.: WO2017/103550
PCT Pub. Date: Jun. 22, 2017

(65) Prior Publication Data
US 2018/0369147 A1 Dec. 27, 2018

(30) Foreign Application Priority Data
Dec. 18, 2015 (FR) .................... 15 62750

(51) Int. Cl.
| | | |
|---|---|---|
| A61K 9/19 | (2006.01) |
| A61K 47/02 | (2006.01) |
| A61K 47/26 | (2006.01) |
| A61K 47/36 | (2006.01) |
| C12N 1/04 | (2006.01) |
| A61P 1/00 | (2006.01) |
| A61K 35/37 | (2015.01) |
| A61K 35/74 | (2015.01) |
| A61K 35/741 | (2015.01) |
| A61K 47/10 | (2017.01) |
| A61K 47/18 | (2017.01) |
| C12Q 1/02 | (2006.01) |
| A61K 35/00 | (2006.01) |

(52) U.S. Cl.
CPC ............ *A61K 9/19* (2013.01); *A61K 35/37* (2013.01); *A61K 35/74* (2013.01); *A61K 35/741* (2013.01); *A61K 47/02* (2013.01); *A61K 47/10* (2013.01); *A61K 47/18* (2013.01); *A61K 47/26* (2013.01); *A61K 47/36* (2013.01); *A61P 1/00* (2018.01); *C12N 1/04* (2013.01); *C12Q 1/02* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 8,460,648 B2 | 6/2013 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,433,651 B2 | 9/2016 | Jones et al. |
| 9,511,099 B2 | 12/2016 | Jones et al. |
| 9,511,100 B2 | 12/2016 | Jones et al. |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 9,642,880 B2 | 5/2017 | Jones et al. |
| 9,649,343 B2 | 5/2017 | Sadowsky et al. |
| 9,675,648 B2 | 6/2017 | Jones et al. |
| 9,682,108 B2 | 6/2017 | Borody |

(Continued)

FOREIGN PATENT DOCUMENTS

| | | |
|---|---|---|
| WO | 02/07741 | 1/2002 |
| WO | 2011122949 | 10/2011 |

(Continued)

OTHER PUBLICATIONS

Strasser, S. et al. J. Appl. Microbiol 2009 vol. 107 pp. 167-177.*
Everard, et al., Cross-talk between Akkermansia muciniphila and intestinal epithelium controls diet-induced obesity, Proc. Natl. Acad. Sci. USA, May 2013, pp. 9066-9077, vol. 110, No. 22.
Sokol, et al., Faecalibacterium prausnitzi is an anti-inflammatory commensal bacterium identified by gut microbiola analysis of Crohn disease patients, Proc. Natl Acad. Sci. USA, Oct. 2008, pp. 16731-16736, No. 105, No. 43.
Tauxe, et al., Fecal Microbiota Transplant Protocol for Clostridium Difficile Infection, Lab Medicine, 2015, pp. 1-8, vo. 46(1).
Van Nood, et al., Fecla microbiota transplantation: facts and controversies, Curr. Opin. Gastroenterol, Jan. 2014, pp. 34-39, vol. 30, No. 1.

(Continued)

*Primary Examiner* — Heidi Reese
(74) *Attorney, Agent, or Firm* — Browdy and Neimark, PLLC (57) ABSTRACT

Method for lyophilisation of a simple of fecal microbiota. The present invention relates to a method for lyophilisation of a sample of fecal microbiota from a donor subject, comprising the following steps: A) mixing of a sample of fecal microbiota from a donor subject with a diluent selected from polyols, disaccharides to pentasaccharides, maltodextrins and mixtures thereof, and B) freezing the mixture obtained in A) at a temperature of less than −50° C., preferably of between −70° C. and −100° C., followed by the lyophilisation thereof.

22 Claims, 1 Drawing Sheet

(56) References Cited

U.S. PATENT DOCUMENTS

| | | | |
|---|---|---|---|
| 9,694,039 | B2 | 7/2017 | Jones et al. |
| 9,737,574 | B2 | 8/2017 | Borody |
| 9,782,445 | B2 | 10/2017 | Jones et al. |
| 9,789,140 | B2 | 10/2017 | Borody |
| 9,855,302 | B2 | 1/2018 | Gajewski et al. |
| 9,867,858 | B2 | 1/2018 | Borody |
| 9,901,603 | B2 | 2/2018 | Borody |
| 9,901,604 | B2 | 2/2018 | Borody |
| 9,962,413 | B2 | 5/2018 | Borody |
| 9,962,414 | B2 | 5/2018 | Borody |
| 2014/0147417 | A1* | 5/2014 | Sadowsky ............ A61K 9/16 424/93.4 |
| 2014/0255351 | A1 | 9/2014 | Berstad et al. |
| 2014/0328803 | A1* | 11/2014 | McKenzie ......... A61K 9/4816 424/93.3 |
| 2014/0363400 | A1 | 12/2014 | Jones et al. |
| 2015/0037285 | A1 | 2/2015 | Blaser et al. |
| 2015/0044173 | A1* | 2/2015 | Jones ................ A61K 35/38 424/93.3 |
| 2015/0216917 | A1 | 8/2015 | Jones et al. |
| 2015/0238545 | A1 | 8/2015 | Borody |
| 2015/0297642 | A1 | 10/2015 | Borody |
| 2016/0296568 | A1 | 10/2016 | Borody |
| 2016/0354414 | A1 | 12/2016 | Jones et al. |
| 2016/0361263 | A1 | 12/2016 | Jones et al. |
| 2017/0049826 | A1 | 2/2017 | Jones et al. |
| 2017/0049827 | A1 | 2/2017 | Jones et al. |
| 2017/0239303 | A1 | 8/2017 | Jones et al. |
| 2017/0246214 | A1 | 8/2017 | Sadowsky et al. |
| 2017/0252303 | A1 | 9/2017 | Jones et al. |
| 2017/0252378 | A1 | 9/2017 | Sadowsky et al. |
| 2017/0258855 | A1 | 9/2017 | Jones et al. |
| 2017/0266239 | A1 | 9/2017 | Borody |
| 2017/0274022 | A1 | 9/2017 | Jones et al. |
| 2017/0281692 | A1 | 10/2017 | Jones et al. |
| 2017/0281693 | A1 | 10/2017 | Jones et al. |
| 2017/0296597 | A1 | 10/2017 | Jones et al. |
| 2018/0000872 | A1 | 1/2018 | Hamilton et al. |
| 2018/0015131 | A1 | 1/2018 | Gajewski et al. |
| 2018/0028573 | A1 | 2/2018 | Sadowsky et al. |
| 2018/0028574 | A1 | 2/2018 | Sadowsky et al. |
| 2018/0028578 | A1 | 2/2018 | Jones et al. |
| 2018/0078586 | A1 | 3/2018 | Jones et al. |
| 2018/0125899 | A1 | 5/2018 | Borody |

FOREIGN PATENT DOCUMENTS

| | | |
|---|---|---|
| WO | 2012/016287 | 2/2012 |
| WO | 2012/122478 | 9/2012 |
| WO | 2013/053836 | 4/2013 |
| WO | 2014/078911 | 5/2014 |
| WO | 2014/121298 | 8/2014 |
| WO | 2014/121301 | 8/2014 |
| WO | 2014/121302 | 8/2014 |
| WO | 2014/121304 | 8/2014 |
| WO | 2014152484 A1 | 9/2014 |
| WO | 2014/176632 | 11/2014 |
| WO | 2014/197562 | 12/2014 |
| WO | 2016/183577 | 11/2016 |
| WO | 2016/196605 | 12/2016 |
| WO | 2016/201114 | 12/2016 |
| WO | 2017/009676 | 1/2017 |
| WO | 2017/075098 | 5/2017 |
| WO | 2018/006088 | 1/2018 |
| WO | 2018/026913 | 2/2018 |

OTHER PUBLICATIONS

Hamilton Matthew J et al: "Standardized Frozen Preparation for Transplantation of Fecal Microbiota for Recurrent Clostridium difficile Infection", American Journal of Gastroenterology, Elsevier Science Inc, pp. 761-767, vol. 107, No. 5, (May 2012).
Anonymous: "Lyophilisation—Wikipedia" (Sep. 10, 2015) URL:https://web.archive.org/web/20150910125419/https://fr.wikipedia.org/wiki/Lyophilisation.

* cited by examiner

METHOD OF LYOPHILIZATION OF A SAMPLE OF FAECAL MICROBIOTA

The present invention relates to a method of lyophilization of a sample of faecal microbiota. The invention also relates to the use of the obtained lyophilizate in the transplantation of faecal microbiota, preferably for treating intestinal dysbioses, in particular *Clostridium difficile* infections.

The human intestinal microbiota is the community of micro-organisms (bacteria, yeasts and fungi) which are found in the human gastro-intestinal system (stomach, bowel and colon). The microbial diversity is currently estimated at approximately $10^3$ bacterial species composing the dominant intestinal microbiota of an adult individual, with an abundance of $10^{14}$ bacteria, representing a dominant bacterial metagenome of 200,000 to 800,000 genes in each individual, i.e. 10 to 50 times the number of genes in the human genome.

The bowel, which is sterile in utero, is colonized from the first days of life until it evolves into a unique individual microbiota. Each person has bacteria that are relatively close in terms of species, but the exact composition of their microbiota (species, proportions) is in large part (more than ⅔ of the species) specific to the host.

Thus, the human intestinal microbiota is an ecosystem that is very diversified, complex and specific to each individual.

It is essential for the health of a individual to maintain a stable microbiota which is both capable of returning to its initial state after a change and is resistant to invasion. The maintenance of a wide diversity of the microbiota promotes its stability. However, certain pathologies or treatments disturb the balance of the microbiota: antibiotics for example, as well as the diseases with an inflammatory component, such as chronic inflammatory bowel diseases (CIBD), can limit the diversity of the microbiota in the bowel.

Antibiotic (or antibiotherapy) treatments in particular, result in a degrading of the microbiota and a loss of its barrier functions, which can promote the proliferation of pathogenic organisms such as *Clostridium difficile*.

*Clostridium difficile* infections are responsible for nosocomial diarrhoeas; this bacterium can present resistances to conventional antibiotherapy (broad-spectrum, such as vancomycin or metronidazole). In order to re-establish the intestinal microbiota, and fight infections of *Clostridium difficile* type, and thus re-establish homeostasis (i.e. symbiosis), the transplantation of faecal microbiota is envisaged and tested. It consists of the introduction of faeces from a healthy donor subject into the alimentary canal of a receiving patient, in order to rebalance the degraded intestinal microbiota of the host. This transplantation of faecal microbiota is in general allogenic (i.e. from a healthy donor individual to a patient). The results obtained on infections of *Clostridium difficile* type are encouraging, and some patients have been treated with success (Tauxe et al, Lab Medicine, Winter 2015, volume 46, Number 1 or van Nood E, Speelman P, Nieuwdorp M, Keller J. 2014 Faecal microbiota transplantation: facts and controversies. Curr Opin Gastroenterol 30(1):34-9).

However, the actual transplantation method is empirical and takes no particular precaution for best preserving the viability of the anaerobic bacteria that are the majority components of the intestinal microbiota. Moreover, the efficacy of the transplantation of faecal microbiota is variable, and can require more than one treatment.

Therefore a need exists to have available samples of faecal microbiota that are safe, effective and easy to obtain, in particular on an industrial scale. Moreover, a need exists for samples of faecal microbiota in which the viability of the bacteria is preserved, and having a long shelf life.

The present invention makes it possible to respond to these needs.

The present invention therefore relates to a method of preparing a lyophilizate of faecal microbiota from a donor subject, comprising the following steps:

A) mixing a sample of faecal microbiota from a donor subject with a diluent chosen from polyols, di- to pentasaccharides, maltodextrins and mixtures thereof, and B) freezing the mixture obtained in A) at a temperature less than −50° C., preferably comprised between −70° C. and −100° C., then lyophilizing it.

In a particular embodiment, the diluent is a saline aqueous solution comprising (i) at least a cryoprotectant chosen from polyols, di- to pentasaccharides, or mixtures thereof, and (ii) maltodextrins.

In another embodiment which can be combined with the preceding embodiment, the diluent is a saline aqueous solution comprising at least galactose-lactose or trehalose as cryoprotectant.

In another embodiment which can be combined with one of the preceding embodiments, the diluent is a saline aqueous solution comprising at least a mixture of maltodextrins as bulking agent, preferably in an amount comprised between 4 and 20% relative to the total volume of the solution.

In another embodiment which can be combined with one of the preceding embodiments, the total amount of cryoprotectant in the saline aqueous solution is comprised between 3 and 30% by weight relative to the total volume of the solution, preferably between 4 and 20% by weight relative to the total volume of the solution.

Preferably, the sample of faecal microbiota used in step A) is purified beforehand.

Preferably, the present invention relates to a method of preparing a lyophilizate of faecal microbiota from a donor subject, comprising the following steps:

A1) optionally, preparing a continuous gradient of iodixanol or 5-(N-2, 3-dihydroxypropylacetamido)-2, 4, 6-tri-iodo-N, N'-bis(2, 3 dihydroxypropyl) isophthalamide formed by freeze-thaw, A2) mixing at least one sample of faecal microbiota from a donor subject with a saline buffer optionally comprising iodixanol or 5-(N-2, 3-dihydroxypropylacetamido)-2, 4, 6-tri-iodo-N, N'-bis(2, 3 dihydroxypropyl) isophthalamide, under anaerobiosis, A3) optionally, forming a deposit of the mixture obtained in A2) under the gradient obtained in A1), A4) sequentially centrifuging at low acceleration under anaerobiosis, or ultracentrifuging the mixture obtained in A2) or A3), A5) recovering the bacterial ring or the supernatant formed on finishing step A4), under anaerobiosis.

A6) mixing the bacterial ring or the supernatant recovered in A5) with a diluent chosen from polyols, di- to pentasaccharides, maltodextrins and mixtures thereof, and B) freezing the mixture obtained in A6) at a temperature less than −50° C., preferably comprised between −70° C. and −100° C., then lyophilizing it.

In such a method, step A1), as well as de facto step A3), are optional.

Such a method is in fact easy to implement, and its effectiveness can be estimated by comparing the microbial population obtained after the method, compared to the initial sample.

The present invention also relates to the use of a lyophilizate of faecal microbiota obtainable by the method according to the invention, as a research tool in functional genomics, metaproteomics or immunology.

For example, the lyophilizate obtainable by the method according to the invention can be used for generating bacterial pellets which, when immobilised in matrices of agarose (or other gels), allow the extraction of DNA fragments of very large size, used for cloning and functional studies. It can also be used for preparing extracts of cytosolic proteins or envelope proteins of bacterial communities with a view to metaproteomic analyses. Finally, it can be used for studying the recognition of intact bacteria by the immune system of the host.

The present invention also relates to the use of a lyophilizate of faecal microbiota from a donor subject obtainable by the method according to the invention, in the autologous or allogenic transplantation of faecal microbiota.

The present invention also relates to the use of a lyophilizate of faecal microbiota from a donor subject obtainable by the method according to the invention, for treating intestinal dysbioses, due to infections and in particular *Clostridium difficile* infections, dysbioses induced by drug treatments, by physical treatments (in particular radiation), by surgical operations (in particular bowel), by colonoscopies or by nutritional intakes. The present invention also relates to the use of a lyophilizate of faecal microbiota from a donor subject obtainable by the method according to the invention, for treating a pathology chosen from the chronic inflammatory bowel diseases (CIBD), functional bowel disorders, obesity, metabolic diseases (in particular type 2 diabetes, metabolic syndrome) and autoimmune diseases (in particular type 1 diabetes), allergies, hepatic diseases (in particular steatosis, cirrhosis), certain neurological diseases (in particular autism) and certain cancers (in particular colorectal cancer).

By intestinal dysbiosis, is meant any sustained imbalance of the intestinal microbiota. By sustained imbalance of the intestinal microbiota, is meant any loss of beneficial micro-organisms, and/or any loss of diversity of micro-organisms, and/or any expansion or development of aggressive micro-organisms among the commensals (pathobionts), and/or any proliferation of pathogenic micro-organisms (in particular *C. difficile*). Any sustained degradation of the human intestinal microbiota can in fact engender or accompany in a chronic fashion a pathological state. In particular, reduction in the diversity within the microbiota is characteristic of diseases associated with a dysbiosis (in particular obesity, Crohn's disease, diabetes or allergy) (Sansonetti, Collège de France, 22 Jan. 2014).

Preferably, the pathology to be treated is an intestinal dysbiosis.

By chronic inflammatory bowel diseases (CIBD), is meant in particular Crohn's disease, ulcerative colitis.

By functional bowel disorders, is meant in particular irritable bowel syndrome, spasmodic colitis.

The method of preparing a lyophilizate of faecal microbiota from a donor subject according to the invention thus comprises the following steps:

A) mixing a sample of faecal microbiota from a donor subject with a diluent chosen from polyols, di- to pentasaccharides, maltodextrins and mixtures thereof, and B) freezing the mixture obtained in A) at a temperature less than −50° C., preferably comprised between −70° C. and −100° C., then lyophilizing it.

Step A) of the method according to the invention comprises mixing a sample of faecal microbiota from a donor subject with a diluent chosen from the cryoprotectants such as polyols, di- to pentasaccharides; bulking agents such as maltodextrins; and mixtures thereof.

Preferably, the sample of faecal microbiota from the donor subject is a sample of faeces from said donor. In fact, the sample of faeces contains the faecal microbiota of the donor subject. Preferably according to the invention, the donor subject is a healthy human subject. By "healthy" subject, is meant a subject not suffering from an imbalance in the intestinal microbiota or from a pathology diagnosed/recognised by the medical profession. Preferably, the sample of faecal microbiota from the donor subject is purified beforehand.

Alternatively, preferably according to the invention, the donor subject is an unwell human subject.

Preferably, the sample of faeces has a mass of at least 20 g.

The sample of faecal microbiota is always obtained and mixed under anaerobiosis (i.e. under an atmosphere devoid of oxygen). Under anaerobiosis, the viability of the constitutive bacteria of the faecal microbiota and present in the sample is therefore preserved.

Preferably, prior to its use, the sample of faecal microbiota is filtered under anaerobiosis. The prior filtration step can comprise, under anaerobiosis, filtration using a Seward bag provided with a filter.

Preferably, the sample of faecal microbiota is taken wider anaerobiosis, using an air-tight collection device: Preferably, this device is in a form of the type comprising:

a container comprising a body which comprises an internal space capable of receiving the sample of faecal microbiota from the donor subject, and a neck which delimits an opening for access to the internal space of the body, and a cover capable of being mounted in a removable and air-tight manner on the neck of the container so as to seal the access opening of the neck and to close the internal space of the body, in which the body of the container is constituted by a flexible pouch, and in which at least one from the container and the cover is provided with an evacuation member capable of evacuating at least a part of the gasses contained in the internal space of the body of the container.

Alternatively, the air-tight collection device is presented in a form of the type comprising:

a container comprising a body which comprises a internal space capable of receiving the sample of faecal microbiota from the donor subject, and a neck which delimits an opening for access to the internal space of the body, and a cover capable of being mounted in a removable and air-tight manner on the neck of the container so as to seal the access opening of the neck and to close the internal space of the body, in which the internal space of the body of the container optionally comprises a chemical device neutralizing oxygen.

The diluent can be chosen from the following compounds:
cryoprotectants such as di- to pentasaccharides, i.e. disaccharides, trisaccharides, quadrisaccharides and pentasaccharides; or polyols, such as glycerol, mannitol, sorbitol, propylene glycol or ethylene glycol, bulking agents, such as the partial hydrolysates of starch, in particular of wheat or of maize, or of fecula, comprising a large amount of maltodextrins,
and mixtures thereof.

Preferably, the diluent is a saline aqueous solution comprising at least a cryoprotectant and/or a bulking agent. Thus, typically, the saline aqueous solution comprises water and physiologically acceptable salts. Typically, the salts are calcium, sodium, potassium or magnesium salts, with chloride, gluconate, acetate or hydrogen carbonate ions.

The saline aqueous solution can also optionally comprise at least one antioxidant. The antioxidant is in particular chosen from ascorbic acid and its salts (ascorbate), tocopherols (in particular α-tocopherol), cysteine and its salified forms (in particular hydrochloride) and mixtures thereof.

Preferably, the saline aqueous solution comprises:
at least one salt chosen from sodium chloride, calcium chloride, magnesium chloride, potassium chloride, sodium gluconate and sodium acetate, and
optionally at least one antioxidant, preferably chosen from sodium L-ascorbate, tocopherols, L-cysteine hydrochloride monohydrate and mixtures thereof.

Typically, the salt is present in the saline aqueous solution at a concentration comprised between 5 and 20 g/L, preferably between 7 and 10 g/L.

Typically, the antioxidant is present in the saline aqueous solution in an amount comprised between 0.3 and 1% by weight relative to the total volume of solution, preferably in an amount comprised between 0.4 and 0.6% by weight relative to the total volume of solution.

Preferably, when the antioxidant is a mixture of sodium L-ascorbate and L-cysteine hydrochloride monohydrate, the sodium L-ascorbate is present in an amount comprised between 0.4 and 0.6% by weight relative to the total volume of solution, and the L-cysteine hydrochloride monohydrate is present in an amount comprised between 0.01 and 0.1% by weight relative to the total volume of solution.

Preferably, the saline aqueous solution comprises at least one cryoprotectant. A cryoprotectant is a substance used for protecting the sample from the damage caused by freezing, in particular due to the formation of ice crystals.

Preferably, the cryoprotectant is chosen from polyols, di- to pentasaccharides (i.e. disaccharides, trisaccharides, quadrisaccharides and pentasaccharides), and mixtures thereof. Preferably, the cryoprotectant is chosen from polyols, tri- and disaccharides and mixtures thereof. More preferentially, the cryoprotectant present in the saline aqueous solution is a disaccharide or a trisaccharide.

Among the polyols that can be used, in particular glycerol, mannitol, sorbitol, but also propylene glycol or ethylene glycol may be mentioned.

Among the di- to pentasaccharides that can be used, dimers, trimers, quadrimers and pentamers of identical or different units may be mentioned, said units being chosen from glucose, fructose, galactose, fucose and N-acetyl-neuraminic acid.

Among the disaccharides that can be used, trehalose or one of its analogues, or saccharose may in particular be mentioned.

These cryoprotectants can be used alone or in a mixture.

Typically, the total amount of cryoprotectant present in the saline aqueous solution is comprised between 3 and 30% by weight relative to the total volume of solution, preferably between 4% and 20% by weight relative to the total volume of solution.

Preferably, the cryoprotectant is chosen from glycerol, mannitol, sorbitol, propylene glycol, ethylene glycol, trehalose and its analogues, saccharose, galactose-lactose and mixtures thereof. More preferentially, the cryoprotectant is galactose-lactose or trehalose.

Preferably, the saline aqueous solution according to the invention comprises at least one bulking agent.

The bulking agent is preferably chosen from the partial hydrolysates of starch or of fecula. The partial hydrolysates of starch, in particular of wheat or of maize, as well as the partial hydrolysates of fecula, for example of potato, comprise a large amount of maltodextrins. The maltodextrins are the result of the partial hydrolysis of starch or of fecula, and are constituted by different sugars (glucose, maltose, maltotriose, oligo- and polysaccharides), the proportions of which vary depending on the degree of hydrolysis.

Preferably, the bulking agent present in the saline aqueous solution is a mixture of maltodextrins, in which the amount of maltodextrins is comprised between 4 and 20% by weight relative to the total volume of solution.

Preferably, step A) is carried out by mixing the sample of faecal microbiota with the diluent, in a weight ratio of microbiota, preferably purified (g)/volume of diluent (mL) comprised between 1:1 and 1:10.

Then the mixture obtained in A) is frozen at a temperature less than −50° C., preferably comprised between −70° C. and −100° C., then subjected to lyophilization: this is step B). It is preferably carried out under the following conditions:

B1) freezing the mixture obtained in A) at a temperature less than −50° C., preferably comprised between −70° C. and −100° C., preferably at a temperature of approximately −80° C., B2) loading the frozen mixture obtained in B1) into a freeze-drier lyophilizer pre-cooled to a temperature comprised between −50° C. and −30° C., at atmospheric pressure, then B3) at least one step of primary drying of the mixture loaded at B2) comprising lowering the pressure to a value comprised between 80 and 200 µbar (preferentially between 100 and 150 µbar) then increasing the temperature of the shelves to a value comprised between −20° C. and +25° C. (preferentially −10° C.) while applying a heating rate comprised between 0.2 and 0.5° C./min. The pressure and temperature values of the shelves are chosen so that that the temperature of the product is maintained below the collapse temperature throughout the sublimation. The parameters are kept constant until the complete elimination of ice from the mixture, then B4) secondary drying of the mixture obtained at B3) comprising lowering the pressure to a value less than or equal to 80 µbar, preferably the lowest value possible for the equipment, and raising the temperature of the shelves to a value comprised between +25° C. and +35° C., preferentially 25° C. at a heating rate comprised between 0.1 and 0.3< C./min, and maintaining it there for between 8 and 15 hours.

Preferably, the freezing of step B1) is carried out at a temperature less than −50° C., preferably comprised between −70° C. and −100° C. Preferably, the freezing temperature is comprised between −70° C. and −100° C.; more preferentially it is approximately −80° C. or approximately −100° C. In order to be frozen, the mixture obtained in A) can be aliquoted beforehand, in order to ensure specimens of constant volume.

The frozen sample is thus loaded into a freeze-drier lyophilizer pre-cooled to a temperature comprised between −50° C. and −30° C., at atmospheric pressure; this is step B2).

Then, the primary drying of the mixture loaded at B2) takes place; this is step B3). It comprises at least one step of primary drying of the mixture loaded at B2) comprising lowering the pressure to a value comprised between 80 and 200 μbar (preferentially between 100 and 150 μbar) then increasing the temperature of the shelves to a value comprised between −20° C. and +25° C. (preferentially −10° C.) while applying a heating rate comprised between 0.2 and 0.5° C./min. The pressure and temperature values of the shelves are chosen in such a way that the temperature of the product is maintained below the collapse temperature throughout sublimation. The parameters are kept constant until the complete elimination of ice from the mixture.

Finally, B4) the secondary drying of the mixture obtained at B3) is carried out. It comprises lowering the pressure to a value less than or equal to 80 μbar, preferably the lowest value possible for the equipment, and raising the temperature of the shelves to a value comprised between +25° C. and +35° C., preferably 25° C. at a heating rate comprised between 0.1 and 0.3° C./min, and maintaining it there for between 8 and 15 hours.

Finally, a lyophilizate according to the invention is obtained in this way.

Preferably, the method according to the invention comprises, in step A), prior steps of treating the sample of faecal microbiota, before mixing it with the diluent.

Thus, preferably, step A) comprises the following sub-steps:

A1) optionally, preparing a continuous gradient of iodixanol or 5-(N-2, 3-dihydroxypropylacetamido)-2, 4, 6-tri-iodo-N, N'-bis(2, 3 dihydroxypropyl) isophthalamide formed by freeze-thaw, A2) mixing at least one sample of faecal microbiota from a donor subject with a saline buffer optionally comprising iodixanol or 5-(N-2, 3-dihydroxypropylacetamido)-2, 4, 6-tri-iodo-N, N'-bis(2, 3 dihydroxypropyl) isophthalamide, under anaerobiosis, A3) optionally, forming a deposit of the mixture obtained in A2) under the gradient obtained in A1), A4) sequentially centrifuging at low acceleration wider anaerobiosis, or ultracentrifuging the mixture obtained in A2) or A3), A5) recovering the bacterial ring or the supernatant formed on finishing step A4), under anaerobiosis, and A6) mixing the bacterial ring or the supernatant recovered in A5) with a diluent chosen from polyols, di- to pentasaccharides, maltodextrins and mixtures thereof.

In such method, step A1), as well as de facto step A3), are optional.

Preferably, the saline buffer used in the different sub-steps described above is an aqueous solution of HEPES comprising sodium chloride, preferably at a concentration comprised between 7 and 15 g/l. Preferably, the HEPES is present at a concentration comprised between 8 and 50 mM, preferably between 9 and 42 mM.

First Alternative

Preferably, according to a first alternative, the method according to the invention comprises the following steps:

A1) preparing a continuous gradient of iodixanol or of 5-(N-2, 3-dihydroxypropylacetamido)-2, 4, 6-tri-iodo-N, N'-bis(2, 3 dihydroxypropyl) isophthalamide formed by freeze-thaw, A2) mixing at least one sample of faecal microbiota from a donor subject with a saline buffer added to an aqueous solution comprising iodixanol or 5-(N-2, 3-dihydroxypropylacetamido)-2, 4, 6-tri-iodo-N, N'-bis(2, 3 dihydroxypropyl) isophthalamide, said saline buffer being preferably an aqueous solution of HEPES comprising sodium chloride, under anaerobiosis, A3) forming a deposit of the mixture obtained in gradient obtained in A1), A4) ultracentrifuging the mixture obtained in A3), for a time comprised between 40 and 50 minutes, at a temperature comprised between 2° C. and 6° C., at an acceleration comprised between 13000 and 16000×g, A5) recovering the bacterial ring formed on finishing step A4), under anaerobiosis, A6) mixing the bacterial ring recovered in A5) with a diluent chosen from polyols, di- to pentasaccharides, maltodextrins and mixtures thereof, and B) freezing the mixture obtained in A6) at a temperature less than −50° C., preferably comprised between −70° C. and −100° C., then lyophilizing it.

Step A1) thus comprises preparing a continuous gradient of iodixanol or 5-(N-2, 3-dihydroxypropylacetamido)-2, 4, 6-tri-iodo-N, N'-bis(2, 3 dihydroxypropyl) isophthalamide formed by freeze-thaw.

By continuous gradient of iodixanol, is meant a continuous gradient of iodixanol with a density ranging from 1.03 to 1.24, preferably ranging from 1.06 to 1.24.

By continuous gradient of 5-(N-2, 3-dihydroxypropylacetamido)-2, 4, 6-tri-iodo-N, N'-bis(2, 3 dihydroxypropyl) isophthalamide, is meant a continuous gradient of 5-(N-2, 3-dihydroxypropylacetamido)-2, 4, 6-tri-iodo-N, N'-bis(2, 3 dihydroxypropyl) isophthalamide with a density ranging from 1.03 to 1.22.

Preferably, this step A1) is carried out according to the following steps:

A1.a) freezing a solution of iodixanol or 5-(N-2, 3-dihydroxypropylacetamido)-2, 4, 6-tri-iodo-N, N'-bis(2, 3 dihydroxypropyl) isophthalamide at a temperature comprised between −70° C. and −100° C. for at least 12 hours. Preferably, said solution is degassed. By degassed solution of iodixanol or 5-(N-2, 3-dihydroxypropylacetamido)-2, 4, 6-tri-iodo-N, N'-bis(2, 3 dihydroxypropyl) isophthalamide, is meant a solution of iodixanol or 5-(N-2, 3-dihydroxypropylacetamido)-2, 4, 6-tri-iodo-N, N'-bis(2, 3 dihydroxypropyl) isophthalamide in which the concentration of dissolved air is reduced, for example under vacuum. This makes it possible to create a micro-anaerobiosis favourable to the survival of the bacteria during the purification method; then A1.b) thawing the solution obtained in A1.a) at ambient temperature for 2 to 4 hours, in order to obtain a continuous gradient of iodixanol or 5-(N-2, 3-dihydroxypropylacetamido)-2, 4, 6-tri-iodo-N, N'-bis(2, 3 dihydroxypropyl) isophthalamide.

Preferably, the solution of iodixanol used in step A1) is a solution having a concentration comprised between 15 and 25%, preferentially around 20%, by weight of iodixanol by volume of solution (w/v). More preferentially, the solution of iodixanol used is obtained by diluting a commercial 60% aqueous solution of iodixanol, marketed under the name OptiPrep (sterile 60% w/v solution of iodixanol in water), 3 times in a saline buffer, preferentially a buffer comprising 15 mM HEPES and 9 g/L of NaCl having a pH of 7.0.

Preferably, the solution of 5-(N-2, 3-dihydroxypropylacetamido)-2, 4, 6-tri-iodo-N, N'-bis(2, 3 dihydroxypropyl) isophthalamide is a solution comprising 20% by weight of 5-(N-2, 3-dihydroxypropylacetamido)-2, 4, 6-tri-iodo-N, N'-bis(2, 3 dihydroxypropyl) isophthalamide by volume of solution (w/v). More preferentially, the 5-(N-2, 3-dihydroxypropylacetamido)-2, 4, 6-tri-iodo-N, N'-bis(2, 3 dihydroxypropyl) isophthalamide used is marketed by Progen Biotechnik under the name Nycodenz.

Preferably, in step A1.a), freezing the solution of iodixanol or of 5-(N-2, 3-dihydroxypropylacetamido)-2, 4, 6-tri-iodo-N, N'-bis(2, 3 dihydroxypropyl) isophthalamide can be carried out for several days, or even 1 month.

Once the continuous gradient of iodixanol or of 5-(N-2, 3-dihydroxypropylacetamido)-2, 4, 6-tri-iodo-N, N'-bis(2, 3 dihydroxypropyl) isophthalamide has been obtained at step A1), the subsequent steps A2), A4) and A5) are carried out under anaerobiosis.

Step A2) comprises mixing at least one sample of faecal microbiota from a donor subject with a saline buffer added to an aqueous solution comprising iodixanol or 5-(N-2, 3-dihydroxypropylacetamido)-2, 4, 6-tri-iodo-N, N'-bis(2, 3 dihydroxypropyl) isophthalamide, under anaerobiosis. Preferably, said saline buffer is an aqueous solution of HEPES comprising sodium chloride. Preferably, the HEPES is present at a concentration comprised between 30 and 50 mM in the saline buffer. Preferably, sodium chloride is present at a concentration comprised between 7 and 15 g/l in the saline buffer. Preferably, the aqueous solution of iodixanol is at a concentration comprised between 50% and 70%, preferably at approximately 60% (w/v). Preferably, the saline buffer:aqueous solution of iodixanol ratio is approximately 1:3.

Preferably, the aqueous solution of 5-(N-2, 3-dihydroxypropylacetamido)-2, 4, 6-tri-iodo-N, N'-bis(2, 3 dihydroxypropyl) isophthalamide is at a concentration of 60% (w/v). Preferably, the saline buffer:aqueous solution of 5-(N-2, 3-dihydroxypropylacetamido)-2, 4, 6-tri-iodo-N, N'-bis(2, 3 dihydroxypropyl) isophthalamide ratio is approximately 1:3.

Thus, according to step A2), the saline buffer is mixed beforehand with an aqueous solution of iodixanol or of 5-(N-2, 3-dihydroxypropylacetamido)-2, 4, 6-tri-iodo-N, N'-bis(2, 3 dihydroxypropyl) isophthalamide; in this way a saline buffer is obtained comprising iodixanol or 5-(N-2, 3-dihydroxypropylacetamido)-2, 4, 6-tri-iodo-N, N'-bis(2, 3 dihydroxypropyl) isophthalamide. Then the resulting mixture is mixed with the sample of faecal microbiota.

Preferably, mixing the sample of faecal microbiota with a saline buffer comprising iodixanol or 5-(N-2, 3-dihydroxypropylacetamido)-2, 4, 6-tri-iodo-N, N'-bis(2, 3 dihydroxypropyl) isophthalamide is carried out in a ratio of 3 to 4 grams of sample to 22 to 30 ml of saline buffer comprising iodixanol or 5-(N-2, 3-dihydroxypropylacetamido)-2, 4, 6-tri-iodo-N, N'-bis(2, 3 dihydroxypropyl) isophthalamide.

Preferably, when the sample of faecal microbiota is filtered between steps A2) and A3), it is subjected to a step of filtering the mixture obtained in A2) under anaerobiosis, in particular by using a Seward bag provided with a filter.

Then, the mixture obtained in A2), optionally filtered, is deposited under the gradient obtained in A1): this is step A3). Step A3) can be carried out under anaerobiosis or under anaerobiosis.

Preferably, the mixture obtained in A2) is present in a syringe provided with a needle, and the gradient of iodixanol or of 5-(N-2, 3-dihydroxypropylacetamido)-2, 4, 6-tri-iodo-N, N'-bis(2, 3 dihydroxypropyl) isophthalamide is present in a container of tube type. In this case, the mixture obtained in A2) is deposited by plunging the needle of the syringe to the bottom of the tube containing the gradient of iodixanol or of 5-(N-2, 3-dihydroxypropylacetamido)-2, 4, 6-tri-iodo-N, N'-bis(2, 3 dihydroxypropyl) isophthalamide, and emptying the content of the syringe.

Then, the preparation obtained in A3) is centrifuged under vacuum in a ultracentrifuge at low acceleration: this is step A4). This ultracentrifuging is carried out for a time comprised between 40 and 50 minutes, at a temperature comprised between 2° C. and 6° C., at a speed comprised between 13000 and 16000×g. Preferably, the ultracentrifuging is carried out for a time comprised between 40 and 50 minutes, at a temperature of approximately 4° C., at a speed of approximately 14500-14600×g.

On finishing this step, a bacterial ring is formed within the gradient. This ring is recovered under anaerobiosis in step A5). It contains the microbiota of interest.

Second Alternative

Preferably, according to a second alternative, the preparation method comprises the following steps:

A2) mixing at least one sample of faecal microbiota from a donor subject with a saline buffer, under anaerobiosis, A4) sequentially centrifuging at low acceleration the mixture obtained in A2), under anaerobiosis, A5) recovering the supernatant formed on finishing step A4), under anaerobiosis, A6) mixing the supernatant recovered in A5) with a diluent chosen from polyols, di- to pentasaccharides, maltodextrins and mixtures thereof, and B) freezing the mixture obtained in A6) at a temperature less than −50° C., preferably comprised between −70° C. and −100° C., then lyophilizing it.

This second alternative comprises a step of sequentially centrifuging at low acceleration. By low acceleration, is meant acceleration comprised between 200 and 500×g. Thus, the different particles present in the sample of faecal microbiota (debris then bacterial cells) will settle.

Step A2) comprises mixing at least one sample of faecal microbiota from a donor subject with a saline buffer, under anaerobiosis. Preferably, said saline buffer is an aqueous solution of HEPES comprising sodium chloride. Preferably, the HEPES is present at a concentration comprised between 5 and 15 mM. Preferably, sodium chloride is present at a concentration comprised between 7 and 15 g/l.

Preferably, mixing the sample of faecal microbiota with a saline buffer is carried out in a sample:buffer weight ratio of 1:20 to 1:25.

Preferably, when the sample of faecal microbiota is filtered between steps A2) and A4), it is subjected to a step of filtering the mixture obtained in A2) under anaerobiosis, in particular by using a Seward bag provided with a filter.

Then, the mixture obtained in A2), optionally filtered, is subjected to sequentially centrifuging at low acceleration, under anaerobiosis: this is step A4).

The sequentially centrifuging at low acceleration of step A4) is preferably carried out at an acceleration comprised between 200 and 500×g for a time comprised between 5 and 15 minutes, at a temperature comprised between 20 and 30° C. More preferentially, the sequentially centrifuging at low acceleration is carried out at an acceleration of approximately 300×g for a time comprised between 5 and 15 minutes, at a temperature comprised between 20 and 25° C.

On finishing this step, the supernatant is recovered under anaerobiosis (step A5)). It contains the microbiota of interest.

Preferably, the sequentially centrifuging at low acceleration of step d) and the step of recovering the subsequent supernatant e) are carried out several times, preferably at least twice, each step d) being carried out at an acceleration comprised between 200 and 500×g for a time comprised between 5 and 15 minutes and at a temperature comprised between 20 and 30° C.

Thus, preferably, in step A5):

A5.1) the supernatant formed on finishing step A4) is recovered,

A5.2) the pellet obtained in A4) is mixed with a saline buffer (the same as that of step A2)), then subjected to sequentially centrifuging at low acceleration as described at step A4), and the supernatant thus obtained is mixed with the supernatant of the fraction A5.1). This operation of washing the pellet can be repeated at will until the pellet is exhausted of bacteria. In practice and for the sake of economy of time and extraction volumes, a single washing of the pellet is typically carried out.

Whatever the method according to the invention (first or second alternative), the latter can comprise the following steps, under anaerobiosis, as step A6):

a) centrifuging the bacterial ring resuspended in a saline buffer or the supernatant obtained in A5), at an acceleration comprised between 3000 and 4000×g for a time comprised between 5 and 15 minutes, at a temperature comprised between 20 and 30° C., b) recovering the pellet obtained on finishing step a), and resuspending in a saline buffer, then centrifuging at an acceleration comprised between 200 and 500×g for a time comprised between 5 and 15 minutes, at a temperature comprised between 20 and 30° C.

c) recovering the supernatant obtained on finishing step b), and resuspending in a saline buffer, then centrifuging at an acceleration comprised between 3000 and 4000×g for a time comprised between 5 and 15 minutes, at a temperature comprised between 20 and 30° C., d) recovering the pellet obtained on finishing step c), and e) mixing the pellet recovered in d) with a diluent chosen from polyols, di- to pentasaccharides, maltodextrins and mixtures thereof.

These steps a) to e) can thus be sub-steps of step A6). Steps a) to d) aim to wash the microbiota obtained in A5). Preferably, the temperature of steps a) to d) is comprised between 20 and 25° C.

Preferably, in these steps a) to d), the saline buffer is an aqueous solution of HEPES comprising sodium chloride, preferably at a concentration comprised between 7 and 15 g/l. Preferably, the HEPES is present at a concentration comprised between 8 and 15 mM.

The pellet obtained at step d) contains the microbiota of interest. It can be mixed with the diluent, as described in step e).

On finishing step A5) or d) (regardless of the methods according to the first or second alternative), the fraction recovered is mixed with a diluent chosen from cryoprotectants such as polyols, di- to pentasaccharides; hulking agents such as maltodextrins; and mixtures thereof.

Then, step B) of freezing and lyophilizing takes place, as described above.

The present invention also relates to the use of a lyophilizate obtainable by the method according to the invention, as research tool, in particular as described above, in functional genomics, metaproteomics or immunology.

The present invention also relates to a lyophilizate of faecal microbiota from a donor subject obtainable by the method according to the invention, for its use in the transplantation of autologous or allogenic faecal microbiota. In fact, the purified lyophilizate of faecal microbiota according to the method of the invention can be administered to the receiving patient.

The receiving patient can be different from the donor subject, and the transplantation is then allogenic.

The receiving patient can also be identical to the donor subject, and the transplantation is then autologous; this type of transplantation can take place when the subject, at the time healthy, gives a sample before degradation of their microbiota. The lyophilizate is then stored, then transplanted into this same subject (receiving patient) if they present in particular a *Clostridium difficile* infection. The transplantation of autologous faecal microbiota has the advantage of avoiding the transmission of a pathogenic agent originating from another donor.

The present invention also relates to a lyophilizate of faecal microbiota from a donor subject obtainable by the method according to the invention, for its use for treating *Clostridium difficile* infections. The present invention also relates to a lyophilizate of faecal microbiota from a donor subject obtainable by the method according to the invention, for its use for accompanying the treatment or for treating a pathology chosen from chronic inflammatory bowel diseases (CIBD), functional bowel disorders, obesity, metabolic diseases and auto-immune diseases, allergies, neurological diseases and cancers. The present invention also relates to a lyophilizate obtainable by the method according to the invention, for its use for limiting the side effects of a treatment chosen from antibiotherapies, chemotherapies, radiotherapies and surgeries in particular of the digestive system.

The lyophilizate obtainable by the method according to the invention has good viability of the bacteria present, as demonstrated in Example 4.

Typically, the viability of the bacteria of the faecal microbiota is measured by staining with the LIVE/DEAD® BacLight™ Bacterial Viability Kit marketed by ThermoFisher Scientific. This kit in fact makes it possible to distinguish living and dead bacteria based on the integrity of their membranes, using two fluorophores, SYTO9® and propidium iodide (PI). The first penetrates into all the cells, intact or not, fixes to the DNA and emits at 540 nm (green) after excitation at 470 nm (blue laser). The PI also targets the DNA, but only penetrates into the cells the membranes of which are damaged; it emits at 635 nm (red) after excitation at 470 nm. Such a kit can be combined with flow cytometry or epifluorescence microscopy.

Preferably, staining the bacteria with the mixture of two SYTO9®/PI fluorophores is carried out under anaerobiosis.

The invention will now be exemplified using the following examples, which are non-limitative.

EXAMPLE 1: PURIFICATION OF A SAMPLE OF FAECAL MICROBIOTA FROM A DONOR SUBJECT BY CONTINUOUS GRADIENT OF IODIXANOL (OPTIPREP) ACCORDING TO THE INVENTION

Principle:

Separation of the total bacterial fraction, by buoyancy within a continuous gradient of OptiPrep auto-formed by freeze-thaw. The heavy faecal dilution in OptiPrep is deposited under a continuous gradient of OptiPrep, pre-formed by freeze-thaw. During centrifuging, the bacteria rise within the gradient up to their buoyant density (1.110-1.190), while the food and endogenous debris sink to the bottom of the gradient. All of the method is under anaerobiosis.

Materials & Methods:
Hepes-NaCl Buffers

|  | NaCl | Hepes | QS MilliQ |
|---|---|---|---|
| For diluent for faecal suspensions 40 mM Hepes-9 g/L NaCl The diluent for faecal suspensions finally comprises, for 100 ml: 25 mL of 40 mM Hepes-9 g/L NaCl and 75 mL of OptiPrep-60 (commercial solution at 60% iodixanol in water) | 0.9 g | 953.2 mg | QS <100 mL then adjust pH to 7.0 then QS 100 mL |
| For gradients 15 mM Hepes-9 g/L NaCl The diluent for gradients ("OptiPrep-20") is finally a dilution of 3 times OptiPrep-60 in 15 mM Hepes-9 g/L NaCl | 0.9 g | 357.5 mg | Qs <100 mL then adjust pH to 7.0 then QS 100 mL |
| For bacterial phase washings 10 mM Hepes-9 g/L NaCl | 18.0 g | 4.766 g | QS <2 L then adjust pH to 7.0 then QS 2 L |

Preparation of the Continuous Gradients by Freeze-Thaw (Step A1)):
  pipette 16 mL of degassed OptiPrep-20 solution, and transfer into tube while avoiding aerating the solution
  freeze the tubes overnight at 80° C.
  thaw the undisturbed, immobile tubes at ambient temperature for 2-3 hours before use; a continuous density gradient of 1.03-1.22 forms automatically.

Preparation of the Faecal Dilutions in an Anaerobic Chamber (Step A2)):
  Put the sample of faeces in the anaerobic chamber
  Weigh on the balance, on which a double filtered sterile Seward bag is placed, the desired weight of faeces (maximum 3.5 g for 1 gradient, possibly less; in this case make up to 3.5 g with 10 mM Hepes—9 NaCl buffer)
  Add 24 mL of diluent for faecal suspensions in the filter of the Seward bag,
  Homogenize the mixture
  Transfer the filtered homogenized faecal suspension into a 50 mL Falcon type tube
  From this tube, fill a 20 mL syringe equipped with a needle with the faecal dilution Producing the Gradient Outside of the Anaerobic Chamber (Steps A3) and A4)):
  Plunge the needle of the syringe obtained in A2) to the bottom of the gradient pre-formed by freeze-thaw obtained in A1)
  Gently load the 20 mL of faecal dilution under the pre-formed gradient
  Recommence for the other gradients
  Weigh all the tubes and adjust the tubes in pairs to exactly the same weight with 10 mM Hepes—9 g/L NaCl buffer
  Carefully insert the tubes into the cold centrifuging buckets for the oscillating rotor
  Centrifuge for 45 min at 4° C. 14,567×g Recovering and Washing the Bacterial Cells in an Anaerobic Chamber (Steps A5), A6) and a) to d)):
  Insert the centrifuging buckets into the anaerobic chamber without opening them
  Open a bucket
  Using a pipette, remove the upper phase
  Pipette the intermediate cellular phase and distribute it into two 50 mL Falcon tubes
  Add washing buffer (10 mM Hepes—9 g/L NaCl) up to graduation 50 of the two Falcon tubes
  Remove the bacterial phases of all the gradients in the same way
  Centrifuge for 10 min 4000×g 22° C. in the oscillating rotor
  Remove the supernatant by aspiration
  Add the washing buffer up to graduation ~25 mL of the Falcon tubes
  Carefully resuspend the bacteria by using a pipette; make up to 50 mL
  Centrifuge for 5 min 300×g 22° C. in the oscillating rotor in order to remove the residual debris
  Transfer the supernatant (containing the bacteria without residue) with a pipette into two new 50 mL Falcons; discard the pellet of debris
  Centrifuge for 10 min 3500×g 22° C. in the oscillating rotor
  Remove the supernatants
  The bacterial pellet without residue obtained can be resuspended in the chosen excipient.

EXAMPLE 2: PURIFICATION OF A SAMPLE OF FAECAL MICROBIOTA FROM A DONOR SUBJECT BY SEQUENTIALLY CENTRIFUGING AT LOW ACCELERATION ACCORDING TO THE INVENTION

Principle:
Separation of the total bacterial fraction, by sequentially centrifuging at low acceleration.
Materials & Methods:
Hepes-NaCl Buffer

|  | NaCl | Hepes | QS MilliQ |
|---|---|---|---|
| for faecal suspensions and washings of bacterial phases 10 mM Hepes-9 g/L NaCl | 18.0 g | 4.766 g | QS <2 L then adjust pH to 7.0 then QS 2 L |

Preparation of the Faecal Dilutions in an Anaerobic Chamber:
  Put the sample of faeces in the anaerobic chamber
  Transfer the desired weight of faeces into the filter of the Seward bag
  Make up QS 350 g with 10 mM Hepes—9 g/L NaCl for 14 g of faeces (i.e. a 1:25 dilution) and homogenize (step b))

Transfer 50 mL of filtered homogenized faecal suspension into six 50 mL Falcon type tubes Centrifuge for 10 min 300×g 22° C. in the oscillating rotor in order to remove the debris (step d))

Distribute the supernatants (they contain the bacteria) into twelve new 50 mL tubes (~25 mL/tube)

Resuspend the 6 pellets in 50 mL 10 mM Hepes—9 g/L NaCl and centrifuge for 10 min 300×g 22° C. in the oscillating rotor (step d))

Distribute the 6 new supernatants into the waiting 12 tubes already containing the first supernatants; QS 50 mL for the 12 tubes with 10 mM Hepes—9 g/L NaCl Centrifuge the 12 tubes for 10 min 3500×g 22° C. in oscillating rotor in order to pellet the bacteria Using a pipette, carefully remove the supernatant Finally, the bacterial pellets without residue obtained are resuspended in the chosen excipient.

EXAMPLE 3: OBTAINING LYOPHILIZATES OF FAECAL MICROBIOTA OBTAINED IN EXAMPLES 1 AND 2

The fractions obtained at the end of the methods of Examples 1 and 2 were mixed with the following diluents:
NaCl: 9 g/L
Maltodextrins: trehalose 15/5 or 5/15 in 9 g/mL NaCl
Iodixanol: commercial aqueous solution at 60% diluted 3 times in 40 mM Hepes—9 g/L NaCl buffer Then they were frozen at −80° C. or −100° C.
Then they were subjected to the following lyophilization cycle:

| Stages | Temperature of shelves | Gradient in min | Pressure µbar | Step in min |
|---|---|---|---|---|
| Pre-cooling | −40° C. | 60 | atmo | Until loading |
| Primary drying | −10° C. | 360 | 150 | 1080 |
| Primary drying | +25° C. | 120 | 150 | 720 |

Secondary drying is carried out at +25° C., at a pressure of 80 µbar for approximately 900 minutes.

The lyophilizer was pre-cooled to −40° C. before loading. From the moment of receiving the samples, the flasks stored in dry ice were loaded into the device and the lyophilizer was placed under vacuum from the end of loading. Two PT100 temperature probes were placed in two flasks. As the products were frozen before loading, the probes are above the product and not in the product.

The duration of the cycle is 45 h. At the end of the cycle, the flasks are stoppered under vacuum in the lyophilizer then capped after unloading.

EXAMPLE 4: VIABILITY OF THE BACTERIA PRESENT IN THE LYOPHILIZATES OF FAECAL MICROBIOTA OBTAINED IN EXAMPLE 3

Protocol:

The viability of the bacteria present in the lyophilizates of faecal microbiota obtained in Example 3 was measured according to the following protocol:

successive decimal dilutions under an anaerobic atmosphere, in order to achieve a final dilution of around $10^6$ bacteria/mL in the sample intended for staining; this operation must be immediately consecutive to resuspending the bacterial pellets without residue in the chosen excipient; the staining of the last dilution must also be immediate, Less than 30 min must elapse between the resuspending and the staining, as the living populations proliferate rapidly if the excipient contains a nutritive substrate: over a 4 hour wait at ambient temperature, under anaerobiosis and in the presence of a single nutritive substrate, the population increases by a half-log and the percentage of bacteria increases by 10%, staining the bacteria, using the LIVE/DEAD® BacLight™ Bacterial Viability Kit according to the manufacturer's instructions, quantification of the living and dead bacteria by flow cytometry: the time between the staining and the quantification must not exceed 20 minutes, whether the stained samples (always shaded from the light) wait at ambient temperature or on crushed ice.

Results:

The results are shown in the table below:

| Sample | Viability 1 week after lyophilization | Standard deviation | Viability 1 month after lyophilization | Standard deviation | Viability 3 months after lyophilization | Standard deviation |
|---|---|---|---|---|---|---|
| Lyophilizate with NaCl | 8.50% | 2.50% | 5.70% | 3.00% | 12.10% | 3.10% |
| Lyophilizate with maltodextrins | 44.80% | 8.00% | 48.10% | 5.80% | 50.20% | 2.20% |
| Lyophilizate with trehalose | 31.10% | 6.80% | 37.60% | 6.90% | 40.30% | 9.80% |
| Lyophilizate with iodixanol | 45.30% | 6.60% | 32.50% | 15.40% | 22.20% | 9.70% |

Thus, the results show that the viability of the bacteria present in the purified samples according to the invention is very good when the bacteria are lyophilized with maltodextrins.

EXAMPLE 5: OBTAINING AND VIABILITY OF BACTERIA PRESENT IN NON-PURIFIED LYOPHILIZATES OF FAECAL MICROBIOTA

A microbiota was collected and suspended in the following solutions:
NaCl: 9 g/L
Maltodextrins: trehalose 15/5 or 5/15 in 9 g/L NaCl
Then the suspensions were frozen at −80° C. or −100° C.

Then they were subjected to the following lyophilization cycle:

| Stages | Temperature of shelves | Gradient in min | Pressure µbar | Step in min |
|---|---|---|---|---|
| Pre-cooling | −45° C. | 60 | atmo | Until loading |
| Primary drying | −10° C. | 360 | 150 | 1080 |
| Primary drying | +25° C. | 60 | 150 | 480 |
| Secondary drying | +25° C. | 1 | 80 | 960 |

The lyophilizer was pre-cooled to −45° C. before loading. On receiving the samples, the stored products in dry ice were loaded into the device and the lyophilizer was placed under vacuum from the end of loading.

The duration of the cycle is 48 h. At the end of the cycle, the flasks are stoppered under vacuum in the lyophilizer then capped after unloading.

Figure 1:
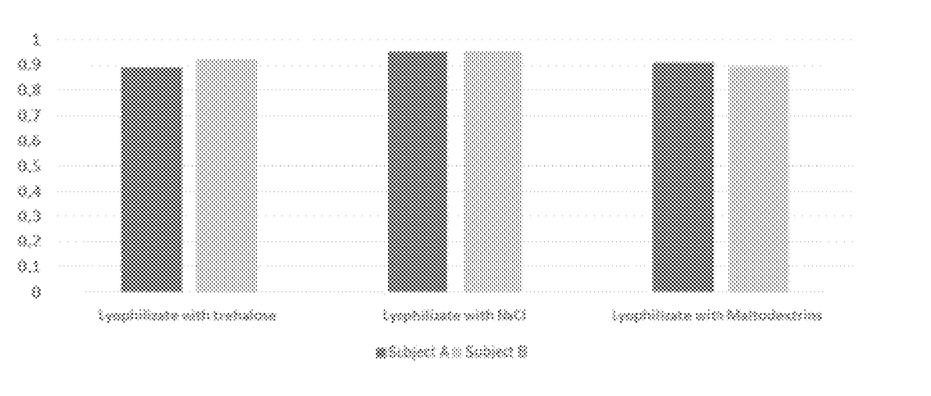
FIG. 1 is a diagram which shows the Pearson correlations between lyophilizates and raw faeces.

The quality of the bacterial populations was assessed in terms of diversity via an extraction of DNA and its analysis by sequencing the rDNA 16S gene. A phylogenetic analysis was then carried out in order to establish the profiles of the different samples in order to compare them. The results are shown in FIG. 1.

Thus, the results show that the correlation levels between the taxonomic profiles are very high for the 3 formulations, demonstrating that the method effectively preserves approximately 90% of the bacterial populations.

The viability was assessed in the same way as that presented in Example 4 and the results after storage for 10 months are presented below:

|  | Subject A | Subject B |
|---|---|---|
| Lyophilizate with trehalose | 24.90% | 31.20% |
| Lyophilizate with NaCl | 11.30% | 20.20% |
| Lyophilizate with Maltodextrins | 33.80% | 30.70% |

After 10 months, the suspensions produced with NaCl have viabilities clearly lower than the other 2.

Thus, the microbiotas obtained according to the method make it possible at the same time to preserve the bacterial populations, since the correlations of the phylogenetic profiles are very high, and in addition they make it possible to store the bacteria alive for longer than the NaCl formulation.

The invention claimed is:

1. A method of preparing a lyophilizate of faecal microbiota from a donor subject, comprising the following steps:
A) mixing a sample of faecal microbiota from a donor subject with a diluent which is a saline aqueous solution comprising (i) at least one cryoprotectant chosen from polyols, di- to pentasaccharides, or mixtures thereof, and (ii) a maltodextrins; and
B) freezing the mixture obtained in A) at a temperature less than −50° C., and then lyophilizing the frozen mixture.

2. The method of preparing a lyophilizate according to claim 1, wherein the diluent is a saline aqueous solution comprising at least galactose-lactose or trehalose as cryoprotectant.

3. The method of preparing a lyophilizate according to claim 1, wherein the diluent is a saline aqueous solution comprising at least a mixture of maltodextrins.

4. The method of preparing a lyophilizate according to claim 1, wherein the total amount of cryoprotectant in the saline aqueous solution is between 3 and 30% by weight relative to the total volume of the solution.

5. The method according to claim 1, wherein step A) comprises the following steps:
A1) optionally, preparing a continuous gradient of iodixanol or 5-(N-2, 3-dihydroxypropylacetamido)-2, 4, 6-tri-iodo-N, N'-bis (2, 3 dihydroxypropyl) isophthalamide formed by freeze-thaw;
A2) mixing at least one faecal microbiota sample from a donor subject with a saline buffer optionally comprising iodixanol or 5-(N-2, 3-dihydroxypropylacetamido)-2, 4, 6-tri-iodo-N, N'-bis (2, 3 dihydroxypropyl) isophthalamide, under anaerobiosis; to form a mixture;
A3) optionally, forming a deposit of the mixture obtained in step A2) of the present method under the gradient obtained in step A1) of the present method,
A4) sequentially centrifuging at low acceleration under anaerobiosis, or ultracentrifuging the mixture obtained in step A2) or step A3) of the present method to obtain a bacterial ring and a supernatant;
A5) recovering the bacterial ring or the supernatant formed from finishing step A4) of the present method, under anaerobiosis; and
A6) mixing the bacterial ring or the supernatant recovered in step A5) of the present method with the diluent.

6. The method according to claim 5, wherein step A6) comprises the following steps under anaerobiosis:
a) centrifuging the bacterial ring obtained in step A5) resuspended in a saline buffer or the supernatant obtained in step A5), at an acceleration between 3000 and 4000×g for a time between 5 and 15 minutes, and at a temperature between 20 and 30° C.; to obtain a pellet;
b) recovering the pellet obtained from finishing step a) of the present method, and resuspending in a saline buffer, then centrifuging at an acceleration between 200 and 500×g for a time between 5 and 15 minutes, and at a temperature between 20 and 30° C.; to obtain a supernatant;
c) recovering the supernatant obtained from finishing step b) of the present method, and resuspending in a saline buffer, then centrifuging at an acceleration between 3000 and 4000×g for a time between 5 and 15 minutes, and at a temperature between 20 and 30° C. to obtain a pellet;
d) recovering the pellet obtained from finishing step c) of the present method; and
e) mixing the pellet recovered in d) of the present method with the diluent.

7. The method according to claim 1, wherein the lyophilization of step B) is carried out in the following conditions:
B1) freezing the mixture obtained in A) at a temperature less than −50° C.;
B2) loading the frozen mixture obtained in B1) into a freeze-drier lyophilizer with shelves to a temperature between −50° C. and −30° C., at atmospheric pressure; then
B3) at least one step of primary drying of the mixture loaded at B2) comprising lowering the pressure to a value between 80 and 200 µbar, then increasing the temperature of the shelves to a value between −20° C. and +25° C., while applying a heating rate between 0.2 and 0.5° C./min; then
B4) secondary drying of the mixture obtained at B3) comprising lowering the pressure to a value less than or equal to 80 µbar, and raising the temperature of the shelves to a value comprised between +25° C. and +35° C., at a heating rate comprised between 0.1 and 0.3° C./min, and maintaining the temperature for between 8 and 15 hours.

8. The method according to claim 1, wherein the saline buffer is an aqueous solution of HEPES comprising sodium chloride.

9. The method according to claim 1, which comprises the following steps:
- A1) preparing a continuous gradient of iodixanol or 5-(N-2, 3-dihydroxypropylacetamido)-2, 4, 6-tri-iodo-N, N'-bis (2, 3 dihydroxypropyl) isophthalamide formed by freeze-thaw,
- A2) mixing at least one faecal microbiota sample from a donor subject with a saline buffer added to an aqueous solution comprising iodixanol or 5-(N-2, 3-dihydroxypropylacetamido)-2, 4, 6-tri-iodo-N, N'-bis (2, 3 dihydroxypropyl) isophthalamide, to form a mixture under anaerobiosis,
- A3) forming a deposit of the mixture obtained in A2) under the gradient obtained in A1),
- A4) ultracentrifuging the mixture obtained in A3), for a time between 40 and 50 minutes, at a temperature between 2° C. and 6° C., and at a speed comprised between 13000 and 16000×g to form a bacterial ring,
- A5) recovering the bacterial ring formed from finishing step A4), under anaerobiosis,
- A6) mixing the bacterial ring recovered in A5) with the diluent to form a mixture, and
- B) freezing the mixture obtained in A6) at a temperature less than −50° C., then lyophilizing the mixture.

10. The method according to claim 9, wherein the preparing of a continuous gradient of iodixanol formed by freeze-thaw in step A1) is carried out according to the following steps:
- A1.a) freezing a solution of iodixanol or 5-(N-2, 3-dihydroxypropylacetamido)-2, 4, 6-tri-iodo-N, N'-bis (2, 3 dihydroxypropyl) isophthalamide at a temperature between −70° C. and −100° C. for at least 12 hours; and then
- A1.b) thawing the solution obtained in A1.a) at an ambient temperature for 2 to 4 hours, in order to obtain a continuous gradient of iodixanol or 5-(N-2, 3-dihydroxypropylacetamido)-2, 4, 6-tri-iodo-N, N'-bis (2, 3 dihydroxypropyl) isophthalamide.

11. The method according to claim 1, which comprises the following steps under anaerobiosis:
- A1) mixing at least one sample of faecal microbiota from a donor subject with saline buffer to obtain a mixture;
- A2) sequentially centrifuging at low acceleration the mixture obtained in A1) to obtain a supernatant;
- A3) recovering the supernatant formed from finishing step A2);
- A4) mixing the supernatant recovered in A3) with the diluent to obtain a mixture; and
- B) freezing the mixture obtained in A4) at a temperature less than −50° C., and then lyophilizing the mixture.

12. The method according to claim 11, wherein the sequential centrifugation at low acceleration of step A2) is carried out at an acceleration between 200 and 500×g for a time between 5 and 15 minutes, and at a temperature between 20 and 30° C.

13. A lyophilizate of fecal microbiota from a donor subject obtainable by the method according to claim 1, for use in the transplantation of autologous or allogenic faecal microbiota, or for treating intestinal dysbioses.

14. A functional genomics, metaproteomics or immunology method, the improvement wherein a lyophilizate obtainable by the method according to claim 1 is used therein as a research tool.

15. The method of claim 1, wherein, in step B, freezing the mixture obtained in A) is performed at a temperature between −70° C. and −100° C.

16. The method according to claim 3, wherein the mixture of maltodextrins is in an amount between 4 and 20% relative to the total volume of the solution.

17. The method according to claim 4, wherein the total amount of cryoprotectant in the saline aqueous solution is between 4 and 20% by weight relative to the total volume of the solution.

18. The method according to claim 7, wherein, in step B1), freezing the mixture obtained in A) is performed at a temperature between −70° C. and −100° C.

19. The method according to claim 8, wherein the aqueous solution of HEPES comprising sodium chloride is at a concentration between 7 and 15 g/l.

20. The method according to claim 9, wherein, in step A2), said saline buffer is an aqueous solution of HEPES comprising sodium chloride.

21. The method according to claim 9, wherein, in step B), freezing the mixture obtained in A6) is performed at a temperature between −70° C. and −100° C.

22. The method according to claim 11, wherein, in step B), freezing the mixture obtained in A4) is performed at a temperature between −70° C. and −100° C.

* * * * *